United States Patent
Pelletier et al.

(10) Patent No.: US 8,946,660 B2
(45) Date of Patent: Feb. 3, 2015

(54) DOWNHOLE SOURCES HAVING ENHANCED IR EMISSION

(75) Inventors: Michael T. Pelletier, Houston, TX (US); Christopher M. Jones, Houston, TX (US); Marina L. Morys, Downington, PA (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 13/510,231

(22) PCT Filed: Jun. 16, 2010

(86) PCT No.: PCT/US2010/038747
§ 371 (c)(1),
(2), (4) Date: May 16, 2012

(87) PCT Pub. No.: WO2011/159289
PCT Pub. Date: Dec. 22, 2011

(65) Prior Publication Data
US 2013/0087723 A1    Apr. 11, 2013

(51) Int. Cl.
*H01K 1/00* (2006.01)
*H01K 1/02* (2006.01)
(Continued)

(52) U.S. Cl.
CPC . *G21K 5/00* (2013.01); *H01J 63/00* (2013.01); *H01J 63/02* (2013.01); *H01K 1/32* (2013.01);
(Continued)

(58) Field of Classification Search
CPC . G01N 2201/06186; G21K 5/00; H01J 63/00; H01J 63/02; H01K 1/00; H01K 1/02; H01K 1/24
USPC ............................................. 250/504 R
See application file for complete search history.

(56) References Cited

U.S. PATENT DOCUMENTS

| 223,898 A | * | 1/1880 | Edison | 313/315 |
|---|---|---|---|---|
| 2,757,300 A | * | 7/1956 | Laidig | 313/3 |

(Continued)

FOREIGN PATENT DOCUMENTS

| AU | 2009356978 | 6/2011 |
|---|---|---|
| GB | 177816 | 3/1922 |

(Continued)

OTHER PUBLICATIONS

Adur, Rohan "Using Single Nitrogen-Vacancy Centers in Diamond Nanocrystals for Sensitive Sensing of Weak Magnetic Fields with Nanoscale Resolution", Ohio State Physics Term Paper, circa 2009, 4 pgs.

(Continued)

*Primary Examiner* — Phillip A Johnston
*Assistant Examiner* — Sean Luck
(74) *Attorney, Agent, or Firm* — Krueger Iselin LLP; Benjamin Fite

(57) ABSTRACT

Light sources are provided with enhanced low-frequency (e.g., near infrared) emission. Some disclosed embodiments include a filament and at least one re-radiator element. The filament heats the re-radiator element to a steady-state temperature that is at least one quarter of the filament's absolute temperature. As disclosed herein, the increased surface area provided by the re-radiator element provides enhanced IR radiation from the light source. Patterning or texturing of the surface can further increase the re-radiator element's surface area. Various shapes such as disks, collars, tubes are illustrated and can be combined to customize the spectral emission profile of the light source. Some specific embodiments employ a coating on the bulb as the re-radiator element. The coating can be positioned to occlude light from the filament or to augment light from the filament, depending on the particular application. The various re-radiator elements can be positioned inside or outside the bulb.

9 Claims, 13 Drawing Sheets

(51) Int. Cl.
| | |
|---|---|
| *G21K 5/00* | (2006.01) |
| *H01J 63/00* | (2006.01) |
| *H01J 63/02* | (2006.01) |
| *H01K 1/32* | (2006.01) |
| *H01K 7/00* | (2006.01) |
| *H01K 11/00* | (2006.01) |
| *G01N 21/31* | (2006.01) |
| *G01N 21/35* | (2014.01) |
| *H01K 1/24* | (2006.01) |
| *G01N 21/3577* | (2014.01) |
| *G01N 21/359* | (2014.01) |

(52) U.S. Cl.
CPC .............. *H01K 7/00* (2013.01); *H01K 11/00* (2013.01); *G01N 21/314* (2013.01); *G01N 21/35* (2013.01); *G01N 21/3577* (2013.01); *G01N 21/359* (2013.01)
USPC .................................................. 250/504 R

(56) References Cited

U.S. PATENT DOCUMENTS

| | | | |
|---|---|---|---|
| 2,972,251 A | 2/1961 | Harper | |
| 3,449,546 A * | 6/1969 | Dhoble | 219/216 |
| 4,103,174 A * | 7/1978 | McClatchie et al. | 250/493.1 |
| 4,160,929 A * | 7/1979 | Thorington et al. | 313/112 |
| 4,227,113 A * | 10/1980 | Walsh | 313/112 |
| 4,774,396 A * | 9/1988 | Salit et al. | 219/553 |
| 4,802,761 A | 2/1989 | Bowen et al. | |
| 4,839,516 A | 6/1989 | Freeman et al. | |
| 4,994,671 A | 2/1991 | Safinya et al. | |
| 4,996,421 A | 2/1991 | Rai et al. | |
| 5,161,409 A | 11/1992 | Hughes et al. | |
| 5,166,747 A | 11/1992 | Schroeder et al. | |
| 5,258,620 A | 11/1993 | Sueyasu et al. | |
| 5,284,054 A | 2/1994 | Loebach | |
| 5,341,207 A | 8/1994 | Tank et al. | |
| 5,360,738 A | 11/1994 | Jones et al. | |
| 5,368,669 A * | 11/1994 | Maine et al. | 156/158 |
| 5,621,523 A | 4/1997 | Oobayashi et al. | |
| 5,790,432 A | 8/1998 | Morys | |
| 5,939,717 A | 8/1999 | Mullins | |
| 5,946,641 A | 8/1999 | Morys | |
| 6,040,191 A | 3/2000 | Grow | |
| 6,178,815 B1 | 1/2001 | Felling et al. | |
| 6,181,427 B1 * | 1/2001 | Yarussi et al. | 356/445 |
| 6,268,726 B1 | 7/2001 | Prammer et al. | |
| 6,350,986 B1 | 2/2002 | Mullins et al. | |
| 6,362,619 B2 | 3/2002 | Prammer et al. | |
| 6,403,949 B1 | 6/2002 | Davis et al. | |
| 6,437,326 B1 | 8/2002 | Yamate et al. | |
| 6,465,775 B2 | 10/2002 | Mullins et al. | |
| 6,518,756 B1 | 2/2003 | Morys et al. | |
| 6,583,621 B2 | 6/2003 | Prammer et al. | |
| 6,765,384 B2 | 7/2004 | Morys | |
| 6,768,105 B2 | 7/2004 | Mullins et al. | |
| 6,825,659 B2 | 11/2004 | Prammer et al. | |
| 6,888,127 B2 | 5/2005 | Jones et al. | |
| 6,956,204 B2 | 10/2005 | Dong et al. | |
| 6,967,322 B2 | 11/2005 | Jones et al. | |
| 6,967,722 B2 | 11/2005 | Manning | |
| 6,975,112 B2 | 12/2005 | Morys et al. | |
| 7,095,012 B2 | 8/2006 | Fujisawa et al. | |
| 7,195,731 B2 | 3/2007 | Jones | |
| 7,245,382 B2 | 7/2007 | Ronnekleiv | |
| 7,248,370 B2 | 7/2007 | Jones | |
| 7,251,037 B2 | 7/2007 | Jones | |
| 7,280,214 B2 | 10/2007 | DiFoggio et al. | |
| 7,315,377 B2 | 1/2008 | Holland et al. | |
| 7,337,660 B2 | 3/2008 | Ibrahim et al. | |
| 7,347,267 B2 | 3/2008 | Morys et al. | |
| 7,362,422 B2 | 4/2008 | DiFoggio et al. | |
| 7,423,258 B2 | 9/2008 | DiFoggio et al. | |
| 7,490,428 B2 | 2/2009 | Morys | |
| 7,490,664 B2 | 2/2009 | Skinner et al. | |
| 7,508,506 B2 | 3/2009 | Christian et al. | |
| 7,511,819 B2 | 3/2009 | DiFoggio | |
| 7,511,823 B2 | 3/2009 | Schultz et al. | |
| 7,532,129 B2 | 5/2009 | Radzinski | |
| 7,571,644 B2 | 8/2009 | Ibrahim et al. | |
| 7,579,841 B2 | 8/2009 | San Martin et al. | |
| 7,696,756 B2 | 4/2010 | Morys et al. | |
| 7,697,141 B2 | 4/2010 | Jones et al. | |
| 7,762,131 B2 | 7/2010 | Ibrahim et al. | |
| 7,784,350 B2 | 8/2010 | Pelletier | |
| 7,800,513 B2 | 9/2010 | Morys | |
| 7,938,175 B2 | 5/2011 | Skinner et al. | |
| 7,976,780 B2 | 7/2011 | Elrod et al. | |
| 2002/0105275 A1 * | 8/2002 | Shigeoka | 313/635 |
| 2004/0042228 A1 * | 3/2004 | Mitobe et al. | 362/510 |
| 2004/0069942 A1 | 4/2004 | Fujisawa et al. | |
| 2004/0152028 A1 * | 8/2004 | Singh et al. | 431/328 |
| 2004/0159002 A1 * | 8/2004 | Carlucci et al. | 34/96 |
| 2005/0052105 A1 * | 3/2005 | Schmidt | 313/113 |
| 2005/0099618 A1 | 5/2005 | DiFoggio et al. | |
| 2005/0275349 A1 * | 12/2005 | Krieglmeyer et al. | 313/578 |
| 2006/0038470 A1 * | 2/2006 | Maul et al. | 313/113 |
| 2006/0096493 A1 * | 5/2006 | Swanson | 102/505 |
| 2006/0142955 A1 | 6/2006 | Jones et al. | |
| 2007/0035736 A1 | 2/2007 | Vannuffelen et al. | |
| 2007/0103162 A1 | 5/2007 | Morys et al. | |
| 2008/0093969 A1 * | 4/2008 | Dhenaut et al. | 313/317 |
| 2008/0106176 A1 * | 5/2008 | Andorfer et al. | 313/113 |
| 2008/0297808 A1 | 12/2008 | Riza et al. | |
| 2009/0039786 A1 * | 2/2009 | Schlager et al. | 313/635 |
| 2010/0148787 A1 | 6/2010 | Morys et al. | |
| 2010/0231225 A1 | 9/2010 | Morys et al. | |
| 2010/0265094 A1 | 10/2010 | Zannoni et al. | |
| 2011/0023594 A1 | 2/2011 | Pelletier et al. | |
| 2011/0181870 A1 * | 7/2011 | Penney et al. | 356/72 |
| 2012/0018152 A1 | 1/2012 | Zuilekom et al. | |

FOREIGN PATENT DOCUMENTS

| | | |
|---|---|---|
| GB | 310895 | 10/1930 |
| GB | 1088268 | 10/1967 |
| GB | 2064217 | 6/1981 |
| GB | 2441069 | 2/2008 |
| JP | H0227686 | 1/1990 |
| JP | 2003157807 | 5/2003 |
| WO | WO-2004/003984 | 1/2004 |
| WO | WO-2011/063086 | 5/2011 |
| WO | WO-2011/078869 | 6/2011 |
| WO | WO-2011/153190 | 12/2011 |
| WO | WO-2012/161693 | 11/2012 |

OTHER PUBLICATIONS

Balasubramanian, Gopalakrishnan et al., "Nanoscale Imaging Magnetometry with Diamond Spins under Ambient Conditions", Nature, vol. 455, Oct. 2, 2008, pp. 648-651.
Bittar, Michael S., et al., "A 3D Borehole Imager and a Dielectric Measurement Tool", PCT Appl No. US09/65537, filed Nov. 23, 2009, 13 pgs.
Bittar, Michael S., et al., "A 3D Borehole Imager", U.S. Appl. No. 13/061,759, filed Mar. 2, 2011, 15 pgs.
Bleier, Z et al., "A Monolithic Interferometer for FT-IR Spectroscopy", Spectroscopy, 13 (10), pp. 46-49.
Boudou, J.P. et al., "High Yield Fabrication of Fluorescent Nanodiamonds", Nanotechnology v20 n23, Jun. 10, 2009, 11 pgs.
Dumeige, Y. et al., "Photo-Induced Creation of Nitrogen-Related Color Centers in Diamond Nanocrystals Under Femtosecond Illumination", Elsevier, www.elsevier.com/locate/jlumin, Journal of Luminescence 109 (2004), pp. 61-67.
Faklaris, Orestis et al., "Comparison of the Photoluminescence Properties of Semiconductor Quantum Dots and Non-Blinking Diamond Nanoparticles. Observation of the Diffusion of Diamond Nanoparticlesin Living Cells", J. European Optical Society, v4, 2009, 8 pgs.
Florescu, Marian et al., "Improving Solar Cell Efficiency Using Photonic Band-Gap Materials", ScienceDirect.com, (Jun. 29, 2007), pp. 1599-1610.

(56) References Cited

OTHER PUBLICATIONS

ICX Photonics, "markIR Infrared Emitters", icxphotonics.com, ICx Photonics, pp. 1-2.
Jones, Christopher M., et al., "Spectroscopic Nanosensor Logging Systems and Methods", PCT Appl No. PCT/US11/038693; filed Jun. 1, 2011, 16 pgs.
Lee, Seung W., et al., "A Soluble Photoreactive Polyimide Bearing the Coumarin Chromophore in the Side Group: Photoreaction, Photoinduced Molecular Reorientation, and Liquid-Crystal Alignability in Thin Films", Langmuir 19 (24) 2003, pp. 10381-10389.
PCT International Search Report and Written Opinion, dated Aug. 24, 2010, Appl No. PCT/US10/038747, "Downhole Sources Having Enhanced IR Emission", filed Jun. 16, 2010, 8 pgs.
PCT Int'l Search Report and Written Opinion, dated Jun. 3, 2010, Appl No. PCT/US09/069492, Interferometry-Based Downhole Analysis Tool, filed Dec. 23, 2009, 8 pgs.
Pelletier, Michael T., et al., "Downhole Sources Having Enhanced IR Emission", PCT Appl No. PCT/US10/038747, filed Jun. 16, 2010, "Downhole Sources Having Enhanced IR Emission", Appl No. PCT/US10/038747, "Downhole Sources Having Enhanced IR Emission", filed Jun. 16, 2010, 22 pgs.
Rabeau, J. R., et al., "Single Nitrogen Vacancy Centers in Chemical Vapor Deposited Diamond Nanocrystals", Nano Letters, v7 n11 p. 3433-3437, 2007, Macquarie University, New South Wales 2109, Australia., pp. 1-20.
Simons, J. K., et al., "X-ray Energy Dependent Photochemestry of the Adamantane (C10H16)/Si (111)-7×7 Surface", American Vacuum Society, J. Vac Sci. Technol. A 11(4) Jul./Aug. 1993, pp. 2244-2249.
Sonnefraud, Yannick et al., "25-nm Diamond Crystals Hosting Single NV Color Centers Sorted by Photon-Correlation Near-field Microscopy", Optics Letters, vol. 33, Issue 6, 2008, pp. 611-613.
Tank, V. "Remote Detection and Quantification of Hot Molecular Combustion Products—Experimental Instrumentation and Determination of Optimal Infrared Spectral Micro Windows", Journal of Molecular Structure, vol. 744-747, 3, pp. 235-242.
Tisler, Julia et al., "Fluorescence and Spin Properties of Defects in Single Digit Nanodiamonds", American Chemical Society, ACS Nano v3 n7 p. 1959-1965, 2009, pp. 1959-1965.
Van Der Sar, T. et al., "Nanopositioning of a Diamond Nanocrystal Containing a Single NV Defect Center", Applied Physics Letters v94 n17, 2009, 3 pgs.
Zhang, Wei et al., "Downhole Optical Fluid Analyzer Having Intermittently Driven Filter Wheel", PCT Appl No. US11/37662, filed May 24, 2011, 11 pgs.
Zhang, Wei et al., "Method to Increase the Numbers of Filters per Optical Path in a Downhole Spectrometer", PCT Appl No. PCT/US11/03655, filed May 24, 2011, 12 pgs.
AU First Examination Report, dated Jun. 25, 2012, Appl No. 2009356978, "Interferometry-Based Downhole Analysis Tool", filed Dec. 23, 2009, 4pgs.
PCT International Preliminary Report on Patentability, dated Jul. 5, 2012, Appl No. PCT/US2009/069492, "Interferometry-Based Downhole Analysis Tool", filed Dec. 23, 2009, 7 pgs.
PCT International Preliminary Report on Patentability, dated Jan. 3, 2013, Appl No. PCT/US2010/038747, "Downhole Sources Having Enhanced IR Emission", filed Jun. 16, 2010, 7 pgs.
First Chinese Office Action, dated Feb. 5, 2013, Appl No. 200980157701.3, "Interferometry-Based Downhole Analysis Tool", filed Dec. 23, 2009, 13 pgs.
US Non-Final Office Action, dated Mar. 26, 2013, U.S. Appl. No. 13/147,478, "Interferometry-Based Downhole Analysis Tool", filed Dec. 23, 2009, 18 pgs.
Canadian Examiner Letter, dated Oct. 24, 2012, Appl No. 2,756,285, "Interferometry-Based Downhole Analysis Tool", filed Dec. 23, 2009, 2 pgs.,(Emery Jamieson Dkt No. 16516-177).
US Final Office Action, dated May 31, 2013, U.S. Appl. No. 13/147,478, "Interferometry-Based Downhole Analysis Tool", filed Dec. 23, 2009, 18 pgs.
AU First Examination Report, dated Jun. 24, 2013, Appl No. 2010355321, "Downhole Sources Having Enhanced IR Emission", filed Jun. 6, 2010, 3 pgs.
Supplementary European Search Report, dated Sep. 2, 2013, Appl No. 10853352.2, "Downhole Sources Having Enhanced IR Emissions", filed Jun. 16, 2010, 13 pgs.
US Non-Final Office Action, dated Sep. 24, 2013, U.S. Appl. No. 13/147,478, "Interferometry-Based Downhole Analysis Tool", filed Dec. 23, 2009, 22 pgs.
CA Examiner'S Letter, dated Jul. 31, 2013, Appl No. 2,781,331, "Downhole Sources Having Enhanced IR Emission", filed May 16, 2012, 6 pgs., (EJ Dkt No. 16516-195 CA).
European Search Report, dated Dec. 12, 2013, Appl No. 09852686.6, "Interferometry-Based Downhole Analysis Tool", filed Dec. 23, 2009, 7 pgs.
AU Divisional Application, dated Feb. 4, 2014, AU Appl No. 2014200604, "Downhole Sources Having Enhanced IR Emission", filed Feb. 4, 2014, 35 pgs.
US Final Office Action, dated Apr. 4, 2014, U.S. Appl. No. 13/147,478, "Interferometry-Based Downhole Analysis Tool," filed Aug. 2, 2014, 25 pgs.
US Non-Final Office Action, dated Apr. 25, 2014, U.S. Appl. No. 13/502,805, "Downhole Optical Radiometry Tool," filed Apr. 19, 2012, 19 pgs.

\* cited by examiner

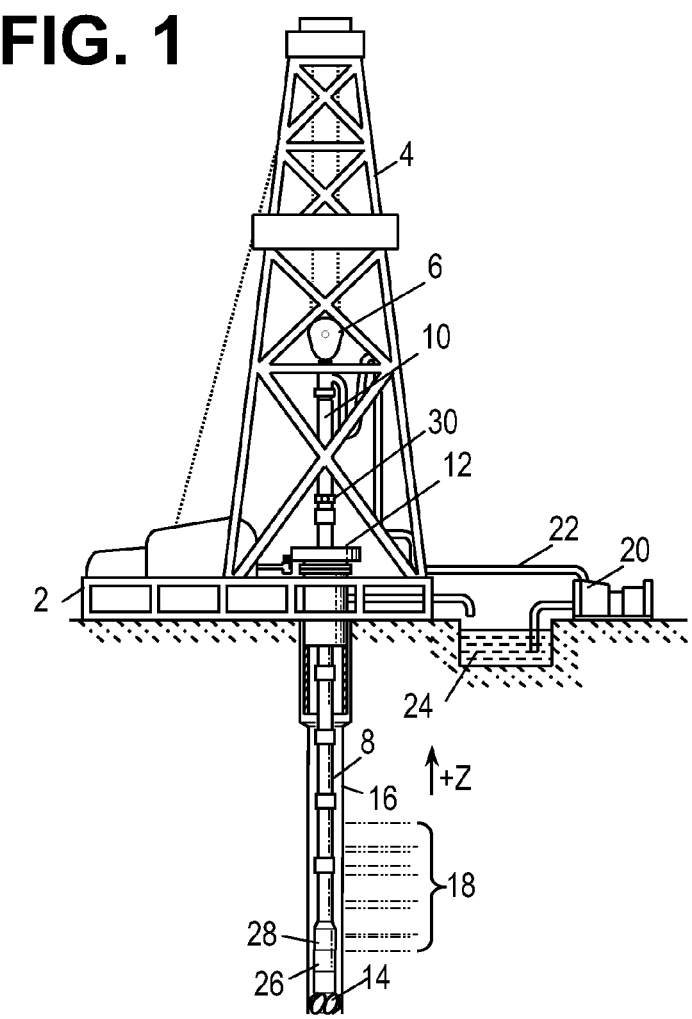
FIG. 1
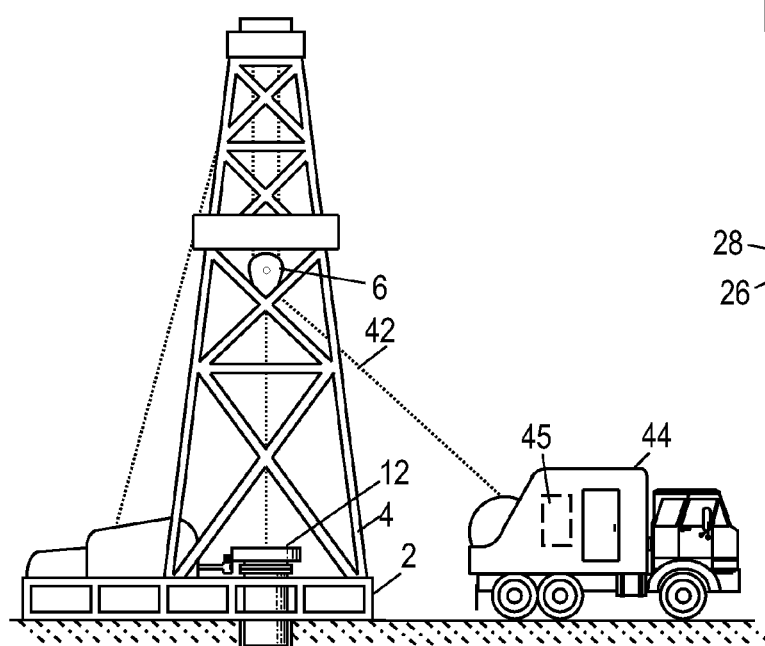
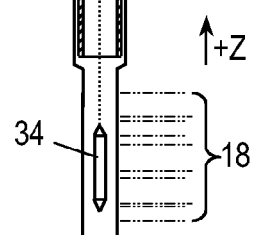
FIG. 2

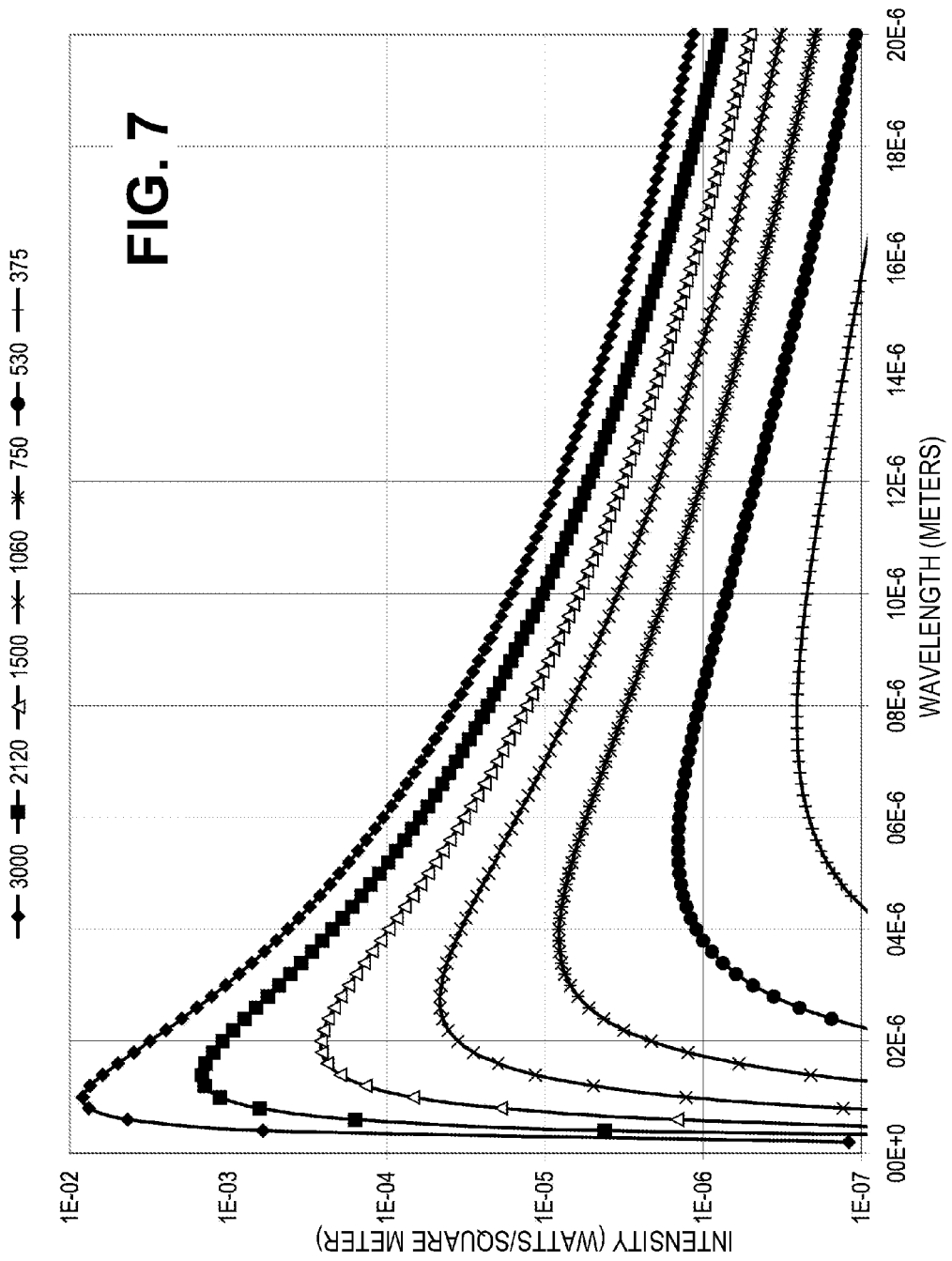

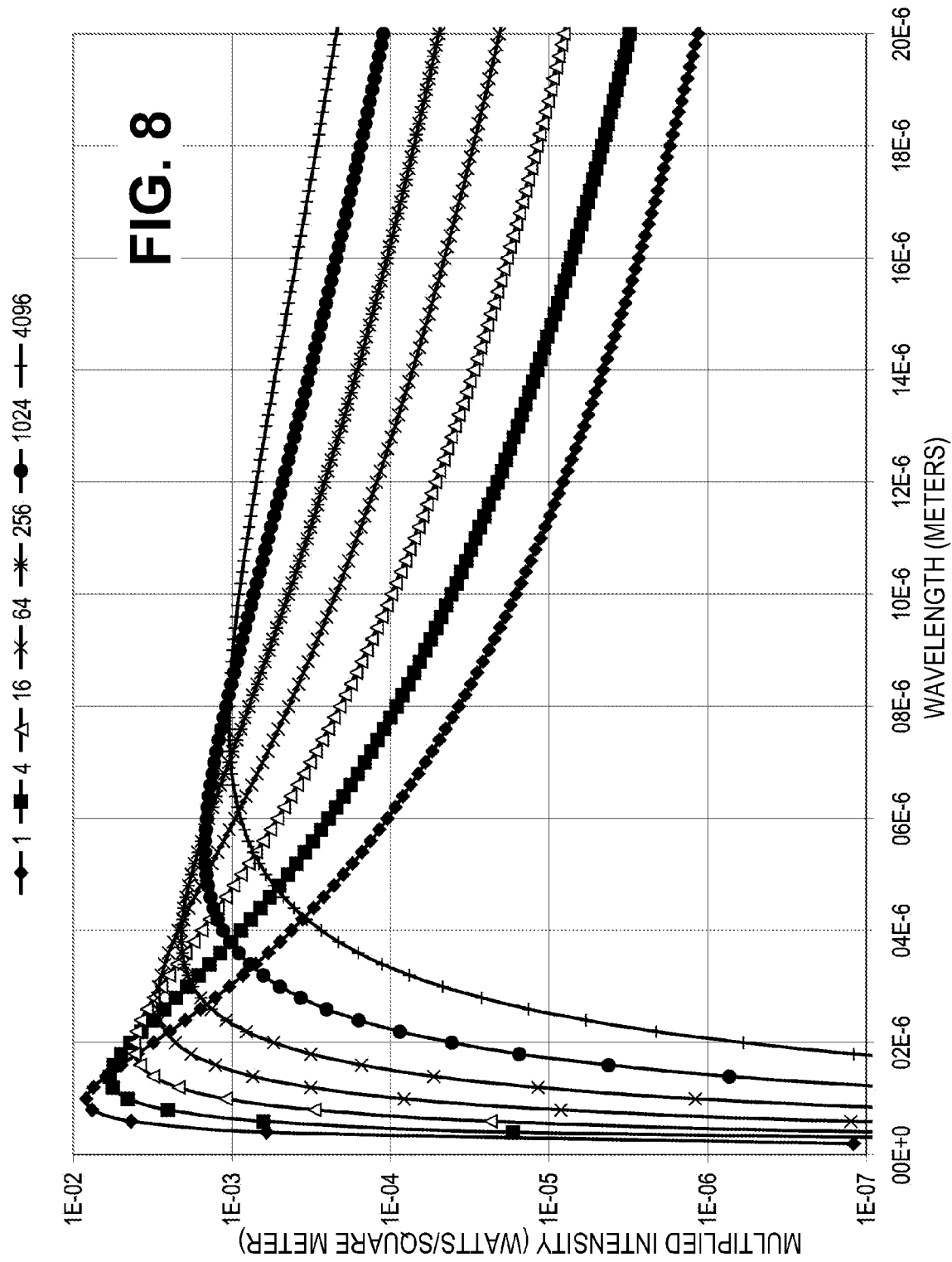

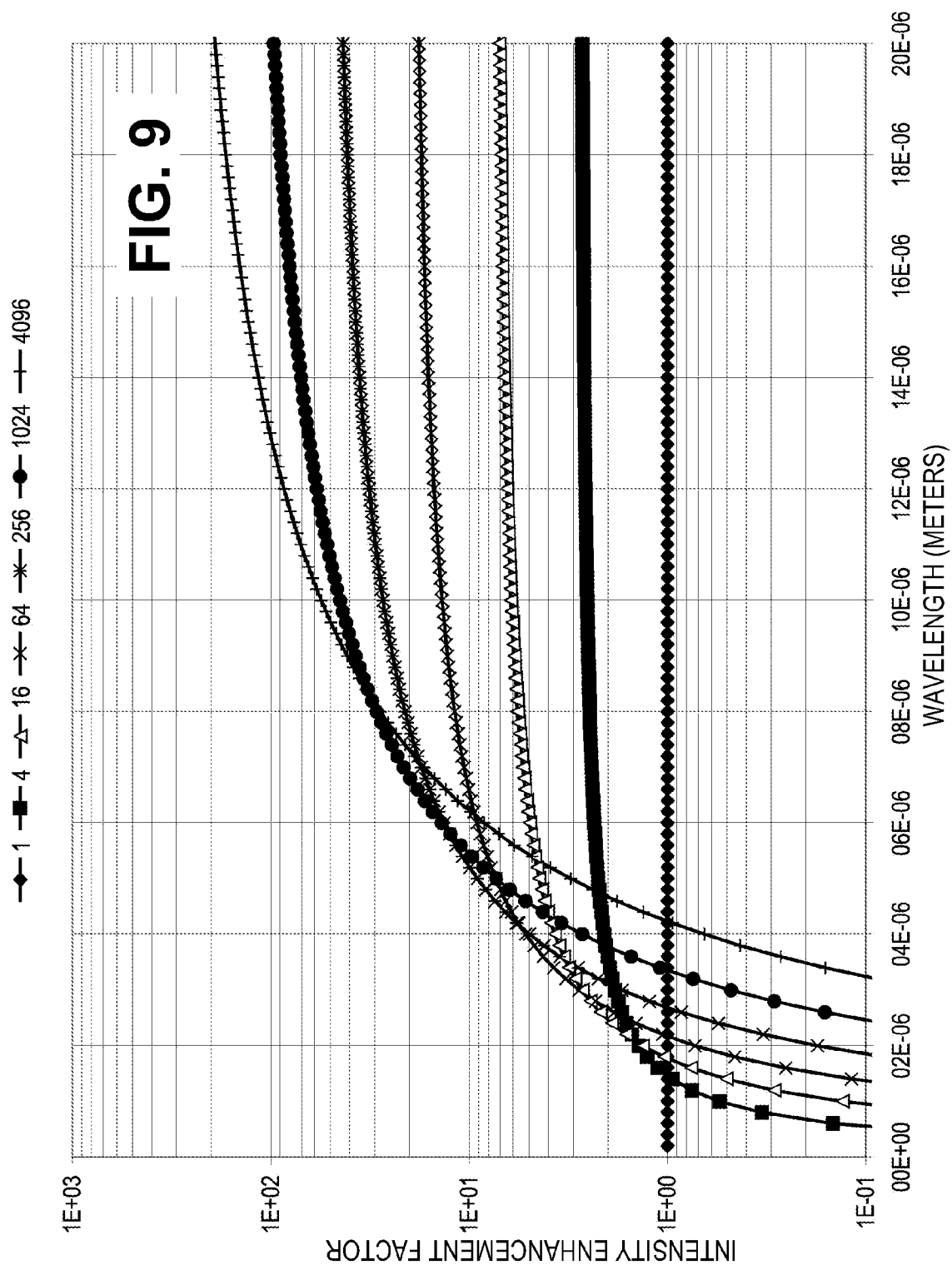

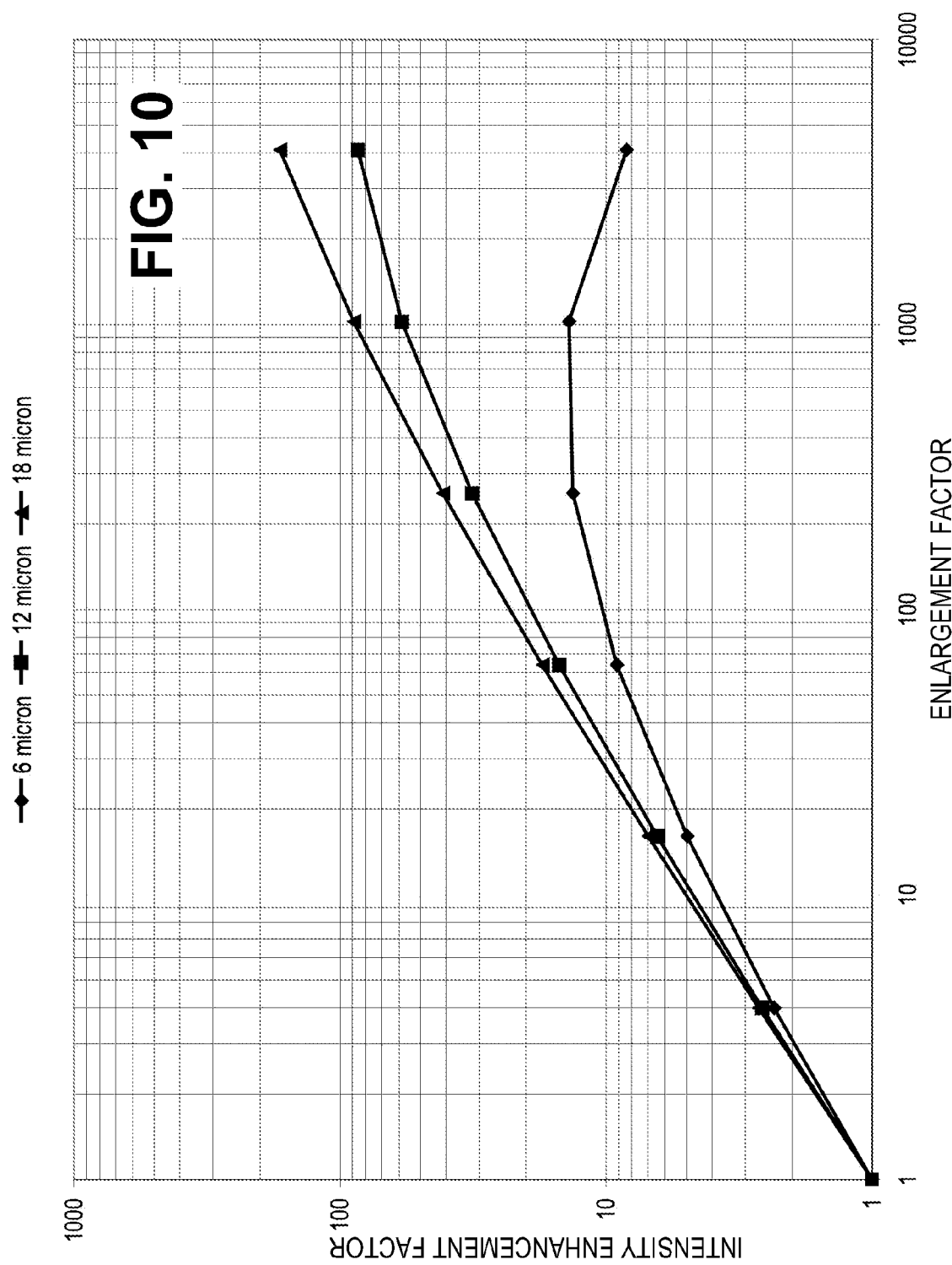

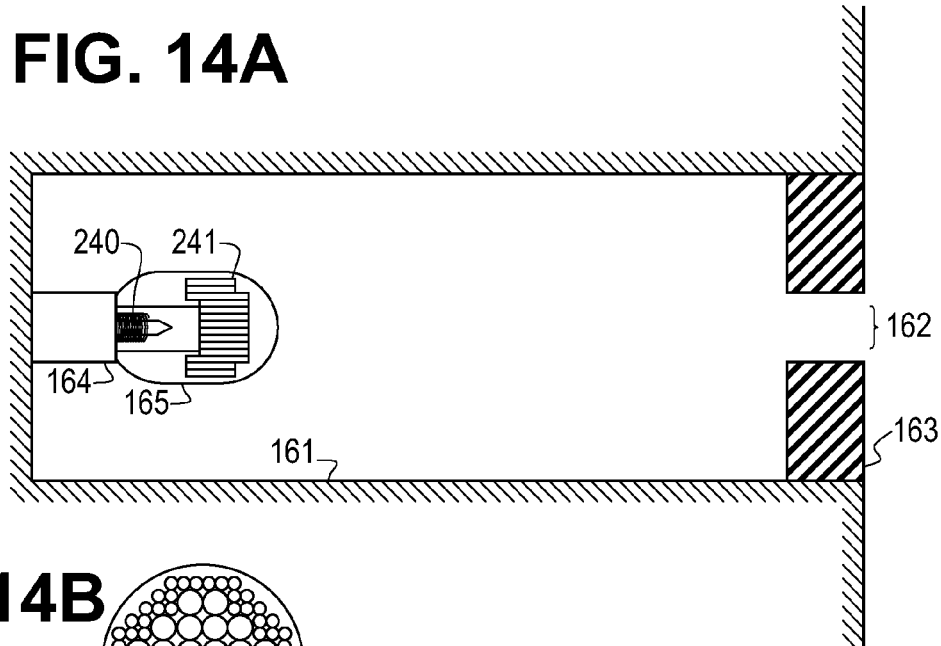
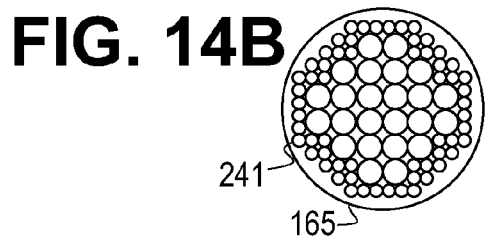
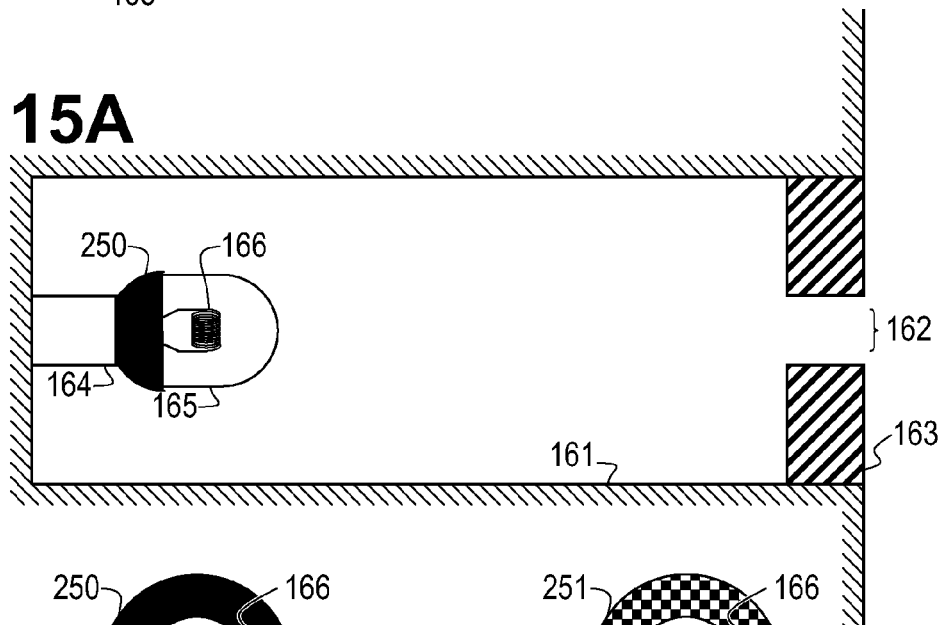
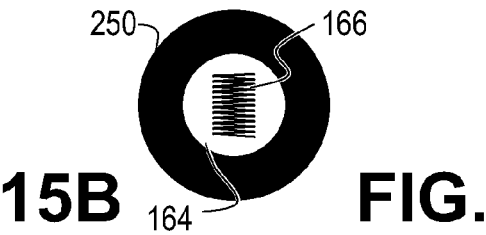
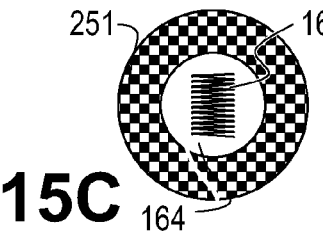

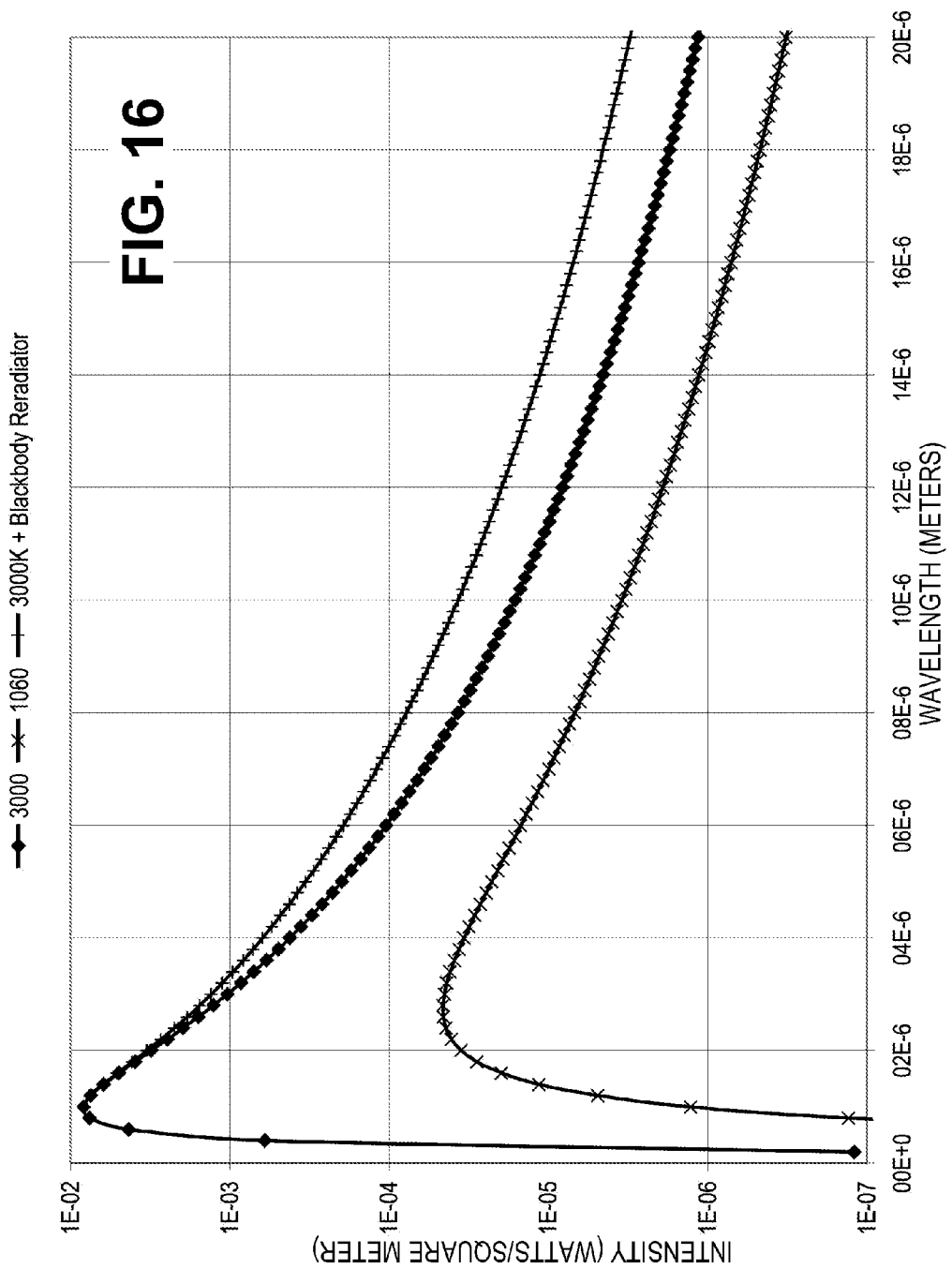

DOWNHOLE SOURCES HAVING ENHANCED IR EMISSION

BACKGROUND

Oil field operators demand access to a great quantity of information regarding the parameters and conditions encountered downhole. A wide variety of logging tools have been and are being developed to collect information relating to such parameters as position and orientation of the bottomhole assembly, environmental conditions in the borehole, and characteristics of the borehole itself as well as the formations being penetrated by the borehole.

A number of these logging tools require a downhole source of illumination, e.g., borehole wall imaging tools, spectral analysis tools, and some types of fluid flow analysis tools. As one particular example, operators often wish to perform downhole formation testing before finalizing a completion and production strategy. Fluid sampling tools enable operators to draw fluid samples directly from the borehole wall and measure contamination levels, compositions, and phases, usually based on the optical properties of the materials drawn into the sample chamber. The light source for such a downhole tool is subject to a number of challenges and restrictions. Often, the energy consumption of the light source is limited, as is the volume which can be set aside for the source. In many cases, the existing light sources are unable to satisfy the combined requirements for a rugged, small volume, broad-spectrum source that includes sufficient intensity for performing spectral analysis in the near-infrared ("NIR").

DESCRIPTION OF THE DRAWINGS

A better understanding of the various disclosed embodiments can be obtained when the following detailed description is considered in conjunction with the attached drawings, in which:

FIG. 1 shows an illustrative environment for logging while drilling ("LWD");

FIG. 2 shows an illustrative environment for wireline logging;

FIG. 7 shows an illustrative series of blackbody radiation curves;

FIG. 8 shows an illustrative series of curves for comparatively larger sources;

FIG. 9 shows an illustrative series of relative enhancement factors;

FIG. 10 shows illustrative enhancement factors for three selected wavelengths;

FIGS. 14A-B show a fourth embodiment of an enhanced light source;

FIGS. 15A-C show a fifth embodiment of an enhanced light source;

FIG. 16 shows an illustrative enhancement curve for an alternative enhancement approach;

Figure 3:
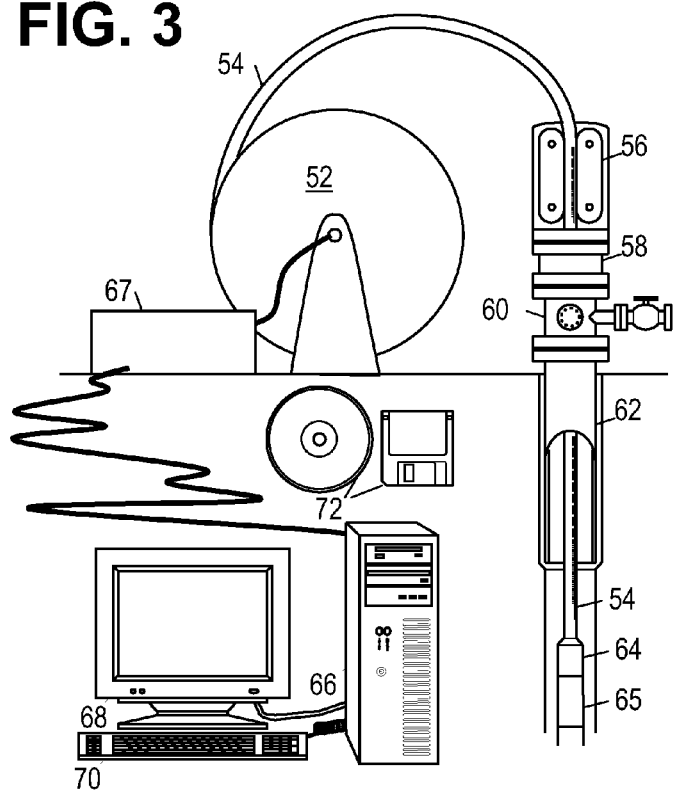
FIG. 3 shows an illustrative environment for tubing-conveyed logging.

While the invention is susceptible to various modifications and alternative forms, specific embodiments thereof are shown by way of example in the drawings and will herein be described in detail. It should be understood, however, that the drawings and detailed description thereto are not intended to limit the disclosure, but on the contrary, the intention is to cover all modifications, equivalents and alternatives falling within the plain-language scope of the claims.

DETAILED DESCRIPTION

Accordingly, there are disclosed herein various methods for providing light sources with enhanced low-frequency (e.g., near infrared) emission, and various illustrative embodiments of such enhanced light sources. Some such embodiments include a filament and at least one re-radiator element. When electrical current is supplied to the filament, it becomes incandescent. The re-radiator element is opaque to at least the peak wavelength of light emitted from the filament, causing the filament to heat the re-radiator to a steady-state temperature that is at least one quarter of an absolute temperature of the filament. As the re-radiator element has a surface area much larger than the filament, it provides enhanced IR radiation from the light source. Patterning or texturing of the surface can further increase the re-radiator element's surface area. Some specific embodiments employ a coating on the bulb as the re-radiator element. The coating can be positioned to occlude light from the filament or to augment light from the filament, depending on the particular application. Other specific embodiments employ disks, collars, tubes and other shapes to customize the spectral emission profile of the light source. The various re-radiator elements can be positioned inside or outside the bulb.

In other disclosed embodiments, the light source includes a base, a filament mounted to the base, and a bulb to enclose the filament in a desired environment (e.g., vacuum, high or low pressure, inert gas, etc.). The filament heats a radiator element mounted within the bulb, the radiator element having a substantially increased surface area relative to that of the filament. In different embodiments, the radiator element is a disk, an arrangement of tubes, or other shape. Multiple radiators can be employed to provide a range of operating temperatures and the corresponding spectral profile that results therefrom.

In yet other disclosed embodiments, a vacuum-tube is provided with a cathode that emits an electron beam and an anode that is heated thereby. The anode is given a radiating area that is a substantial fraction of the available area enclosed by the envelope of the vacuum tube. In some embodiments, the anode comprises an array of tubes having different lengths and sizes to provide a spatially-dependent temperature profile. The tubes can be open on one end and aligned to preferentially emit light along an optical axis.

The disclosed systems and methods are best understood in the context of the larger systems in which they operate. FIG. 1 shows an illustrative logging while drilling (LWD) environment. A drilling platform 2 supports a derrick 4 having a traveling block 6 for raising and lowering a drill string 8. A kelly 10 supports the drill string 8 as it is lowered through a rotary table 12. A drill bit 14 is driven by a downhole motor and/or rotation of the drill string 8. As bit 14 rotates, it creates a borehole 16 that passes through various formations 18. A pump 20 circulates drilling fluid through a feed pipe 22 to kelly 10, downhole through the interior of drill string 8, through orifices in drill bit 14, back to the surface via the annulus around drill string 8, and into a retention pit 24. The drilling fluid transports cuttings from the borehole into the pit 24 and aids in maintaining the borehole integrity.

A LWD tool 26 is integrated into the bottom-hole assembly near the bit 14. As the bit extends the borehole through the formations, logging tool 26 collects measurements relating to various formation properties as well as the tool orientation and various other drilling conditions. The logging tool 26 may take the form of a drill collar, i.e., a thick-walled tubular that provides weight and rigidity to aid the drilling process. As explained further below, tool assembly 26 includes a optical fluid analysis tool that monitors borehole fluid properties. A telemetry sub 28 may be included to transfer measurement data to a surface receiver 30 and to receive commands from the surface. In some embodiments, the telemetry sub 28 does not communicate with the surface, but rather stores logging data for later retrieval at the surface when the logging assembly is recovered.

At various times during the drilling process, the drill string 8 may be removed from the borehole as shown in FIG. 2. Once the drill string has been removed, logging operations can be conducted using a wireline logging tool 34, i.e., a sensing instrument sonde suspended by a cable 42 having conductors for transporting power to the tool and telemetry from the tool to the surface. A wireline logging tool 34 may have pads and/or centralizing springs to maintain the tool near the axis of the borehole as the tool is pulled uphole. As explained further below, tool 34 can include a formation fluid sampler that extends a probe against a borehole wall to draw fluids into a sample analysis chamber. A surface logging facility 44 collects measurements from the logging tool 34, and includes a computer system 45 for processing and storing the measurements gathered by the logging tool.

An alternative logging technique is logging with coil tubing. FIG. 3 shows an illustrative coil tubing-conveyed logging system in which coil tubing 54 is pulled from a spool 52 by a tubing injector 56 and injected into a well through a packer 58 and a blowout preventer 60 into the well 62. (It is also possible to perform drilling in this manner by driving the drill bit with a downhole motor.) In the well, a supervisory sub 64 and one or more logging tools 65 are coupled to the coil tubing 54 and optionally configured to communicate to a surface computer system 66 via information conduits or other telemetry channels. An uphole interface 67 may be provided to exchange communications with the supervisory sub and receive data to be conveyed to the surface computer system 66.

Surface computer system 66 is configured to communicate with supervisory sub 64 during the logging process or alternatively configured to download data from the supervisory sub after the tool assembly is retrieved. Surface computer system 66 is preferably configured by software (shown in FIG. 3 in the form of removable storage media 72) to process the logging tool measurements. System 66 includes a display device 68 and a user-input device 70 to enable a human operator to interact with the system software 72.

In each of the foregoing logging environments, the logging tool assemblies preferably include a navigational sensor package that includes directional sensors for determining the inclination angle, the horizontal angle, and the rotational angle (a.k.a. "tool face angle") of the bottom hole assembly.

As is commonly defined in the art, the inclination angle is the deviation from vertically downward, the horizontal angle is the angle in a horizontal plane from true North, and the tool face angle is the orientation (rotational about the tool axis) angle from the high side of the borehole. In accordance with known techniques, directional measurements can be made as follows: a three axis accelerometer measures the earth's gravitational field vector relative to the tool axis and a point on the circumference of the tool called the "tool face scribe line". (The tool face scribe line is typically drawn on the tool surface as a line parallel to the tool axis.) From this measurement, the inclination and tool face angle of the logging assembly can be determined. Additionally, a three axis magnetometer measures the earth's magnetic field vector in a similar manner. From the combined magnetometer and accelerometer data, the horizontal angle of the logging assembly can be determined. These orientation measurements, when combined with measurements from motion sensors, enable the tool position to be tracked downhole.

In these and other logging environments, measured parameters are usually recorded and displayed in the form of a log, i.e., a two-dimensional graph showing the measured parameter as a function of tool position or depth. In addition to making parameter measurements as a function of depth, some logging tools also provide parameter measurements as a function of rotational angle. Such tool measurements have often been displayed as two-dimensional images of the borehole wall, with one dimension representing tool position or depth, the other dimension representing azimuthal orientation, and the pixel intensity or color representing the parameter value.

Figure 4:
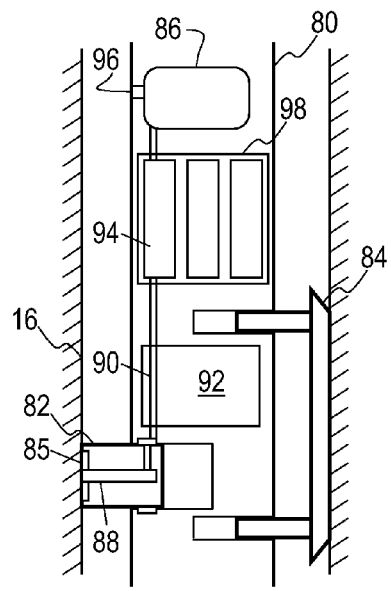
FIG. 4 shows an illustrative formation fluid sampling tool.

FIG. 4 shows an illustrative formation fluid sampler tool 80. Tool 80 can be a drill collar, a coil tubing joint, or a drilling tubular, but most commonly it is expected to be part of a wireline sonde. Tool 80 extends a probe 82 and a foot 84 to contact the borehole wall 16, typically driving them outward from the tool body using hydraulic pressure. The probe 82 and foot 84 cooperate to seat the probe firmly against the borehole wall and establish a seal that keeps borehole fluids from being drawn into the sampling tool. To improve the seal, the wall-contacting face of the probe includes an elastomeric material 85 that conforms to the borehole wall. A pump 86 draws down the pressure, prompting fluid to flow from the formation through a probe channel 88, a sample chamber 90 in fluid analyzer 92, and a sample collection chamber 94. The pump 86 exhausts fluid into the borehole through a port 96 and continues pumping until the sampling process is completed. Typically, the sampling process continues until the tool determines that the sample collection chamber 94 is full and any contaminants have been exhausted. Thereafter the sample collection chamber is sealed and the probe and foot are retracted. If desired, the tool can repeat the process at different positions within the borehole. Sample collection chamber 94 may be one of many such sample collection chambers in a cassette mechanism 98, enabling the tool to return many fluid samples to the surface.

Figure 5:
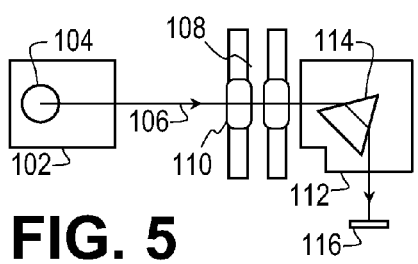
FIG. 5 shows an illustrative fluid spectrum analyzer.

FIG. 5 shows an illustrative spectrum-based fluid analyzer. A collimation apparatus 102 directs light from a broadband light source 104 along an optical path 106 through the analyzer. Light moving along the optical path 106 passes through a sample chamber 108 via windows 110 and thence to a collection apparatus 112 that guides the light to a detector 116. Included within the illustrated collection apparatus is a spectral element 114 such as a prism, diffraction grating, interferometer, filter, multivariate optical element (MOE), or other device that makes the intensity of the light striking a given point on the detector 116 dependent on the spectral characteristics of the fluid in the sample chamber 108. In some embodiments, the spectral element 114 disperses spectral information across an array of sensors in detector 116, while in other embodiments a single sensor in detector 116 measures a time-dependent signal that, through motion or switching of element 114, is indicative of spectral information across a range of frequency values.

Collimation apparatus 102 can take many different forms ranging from a simple aperture to a complex array of lenses and/or reflectors that collect as much light as feasible from the light source 104 and direct it as tightly and uniformly as possible along the optical path 106. Similarly, collection apparatus 114 can take many forms ranging from nothing more than the spectral element 114 itself to a complex array of apertures, lenses, and/or reflectors that guide as much light transmitted, reflected, and/or scattered light from the sample chamber 108 through the spectral element 114 and on to the detector 116.

In different tool embodiments, the material that is to be analyzed can take the form of a gas, fluid, or mixed phase flow captured within a sample cell or flowing past a window. Alternatively, the material can be a solid that is visible through a window or aperture, such as a core sample or a portion of the borehole wall adjacent to the tool. The tool collects transmitted light, reflected light, scattered light, and/or emitted light or fluorescence from the sample and directs it to the detector. The detector can take the form of a photodiode, a thermal detector (including thermopiles and pyroelectric detectors), a Golay cell, or a photoconductive element. Cooling can be employed to improve the signal-to-noise ratio of the detector. The spectrum determined by the tool can be processed downhole to extract the desired information, or it can be stored in memory for later use, possibly in association with a measurement time and/or tool position. The extracted information can be used as the basis for a subsequent tool operation (e.g., the decision to stop pumping after the contamination level drops sufficiently). Illustrative analyses include determining contamination levels in a sampled fluid, identifying fluid composition, identifying fluid type, identifying PVT properties, etc. The composition analysis might include determining concentrations of compounds such as $CO_2$, $H_2S$, etc., or determining hydrocarbon fractions of saturated, aromatics, resins, and asphaltenes. Fluid type determination can be finding volume percentages of oil, water, and gas. PVT properties can include bubble point determination, gas/oil ratio, density variation with pressure, etc. Measurements can be communicated to the surface for display to an operator and further processing.

Various processing techniques are known for determining composition or type information from a spectrum of reflected, transmitted, or scattered light. They include Inverse Least Squares Regression and Principal Component Analysis. However, other techniques can also be used, including correlation of measured interferograms with template interferograms. Various other features can be incorporated into the tool, including outfitting the tool with a reservoir of a reference fluid for downhole calibration of the system and for compensating for contamination on the windows of the flow cell. A shock and vibration monitoring system (e.g., an accelerometer that is mounted to the tool and periodically sensed by the processing electronics) can be used to detect periods of high vibration that might make measurements less reliable. Measurements collected during these periods can be discarded or given a lower weighting that reflects their reduced reliability. Scattered light can be analyzed to determine the size distribution of particles entrained in a fluid flow. An ultraviolet light source can be included to induce fluorescence in the material, which fluorescence can be analyzed to aid in determining composition of the sample. To monitor the spectrum and intensity of the light source, a bypass path can be provided to direct light to a detector without passing through the sample cell. In some embodiments, a collection of varied detector types can be used, with filters, dichroic mirrors or other distribution means used to split the received light into bands best suited to be measured by the individual detectors.

For the purposes of this disclosure, the term "broadband" is used to distinguish the light source from narrowband sources that provide only isolated peaks in their spectrum. The broadband sources contemplated for use downhole have continuous spectrums in the range of 200-400 nm (for UV absorption and fluorescence spectroscopy), 1500-2300 nm (for special purpose spectroscopy, e.g. GOR determination), and 400-6000 nm (for general purpose VIS-IR spectroscopy). These examples are merely illustrative and not limiting. One readily available source suitable for this purpose is a tungsten-halogen incandescent source with a quartz envelope, generating light across the 300-3000 nm range. Tungsten-halogen incandescents with sapphire or zinc selenide envelopes are also contemplated for extended wavelengths ranges. Broadband fluorescent sources, broadband quantum sources, and combined narrowband sources (such as LEDs) may also be suitable. Windows 110 and any lenses in collimation apparatus 102 and collection apparatus 112 should of course be made of a material that is transparent at the desired wavelengths, e.g., for visible and NIR wavelengths, quartz, sapphire, or zinc selenide.

Figure 6:
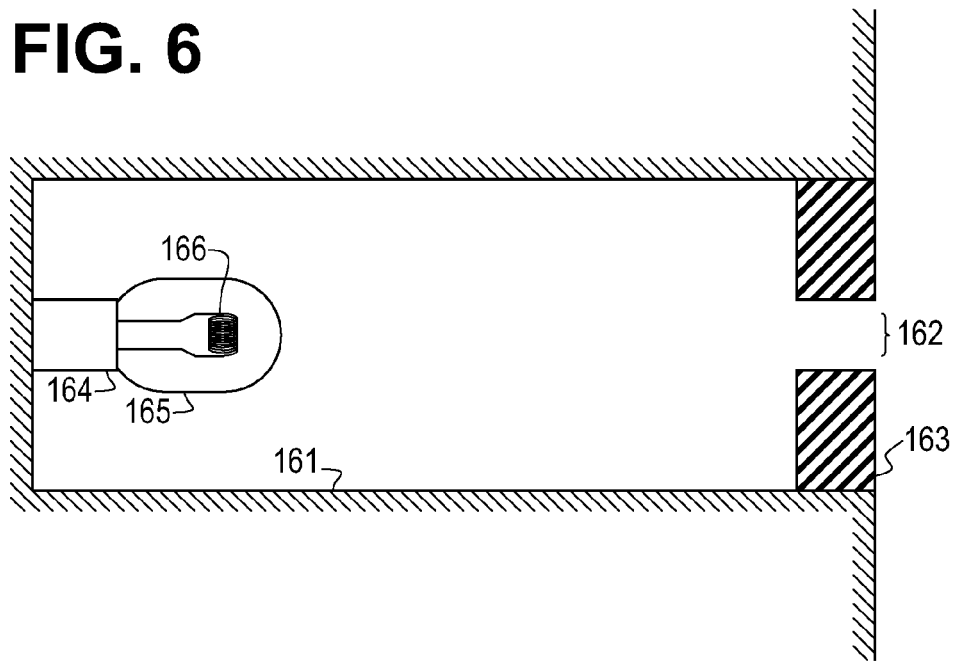
FIG. 6 shows an illustrative baseline light source.

FIG. 6 shows an illustrative light source that will be used as a baseline for comparison with the various enhanced light sources described below. The collimation apparatus 102 takes the form of a bulb compartment 161 having an aperture 162 defined by an aperture plate 163. Aperture 162 is spaced far enough away from the bulb that the emitted light is suitably collimated. Light source 104 take the form of a bulb seated in a socket 164. A bulb envelope 165, made of a suitable material, contains a inert gas with a small amount of a halogen around a tungsten filament 166. Electricity from socket 164 passes through the filament 166, heating it to an operating temperature (e.g., 3000 K) where it radiates light. The spectrum of radiated light essentially corresponds to that of a blackbody radiator.

FIG. 7 shows the blackbody radiation spectrum given by Planck's law for radiators at different temperatures: 3000 K, 2120 K, 1500 K, 1060 K, 750 K, 530 K, and 375 K, over wavelengths ranging from 0 to 20 microns. At any given wavelength (e.g., 12 microns), the source intensity falls as the temperature decreases. (In fact, the Stefan-Boltzmann law teaches that the total radiated power per unit area is proportional to the fourth power of the absolute temperature.) FIG. 7 would seem to indicate that the only way to increase source intensity at a given wavelength would be to increase the power.

The authors have discovered that if the total radiated power is held constant while the surface area of the radiator is increased, a new set of curves is achieved. The increased surface area results in a lower operating temperature in accordance with the Stefan-Boltzmann law. However, this loss in temperature is offset by the increased radiating area. Thus, taking the 3000 K curve from FIG. 7 as a reference, FIG. 8 shows the total intensity when the source area is quadrupled, quadrupled again, etc., resulting in sources having 4, 16, 64, 256, 1024, and 4096 times the original area of the 3000 K reference source. Thus, for a given input power to the source, the long-wavelength radiation intensity can be increased by enlarging the size of the radiating area.

FIG. 9 shows the intensity enhancement factor as a function of wavelength for the different areas. For the reference source, the enhancement factor is unity at all wavelengths. A quadruple-size source loses intensity at wavelengths below 1 micron, but gains at longer wavelengths. At long wavelengths, the enhancement factor approaches 2.83 (for a 183% gain in intensity). At 12 microns, the enhancement factor is 2.59. For a 16× source, the enhancement factor approaches 8 at long wavelengths, and at 12 microns is 6.42. FIG. 10 shows the intensity enhancement factors at wavelengths 6, 12, and 18 microns for the various enlargement factors. It can be seen that at some enlargement factor, the intensity enhancement peaks and begins to decline, depending on the wavelength in question. Generally speaking, these peaks occur at relatively sizeable enlargements (e.g., greater than 100×), so other constraints may play a role in determining the optimum size for the radiating area.

Figure 11:
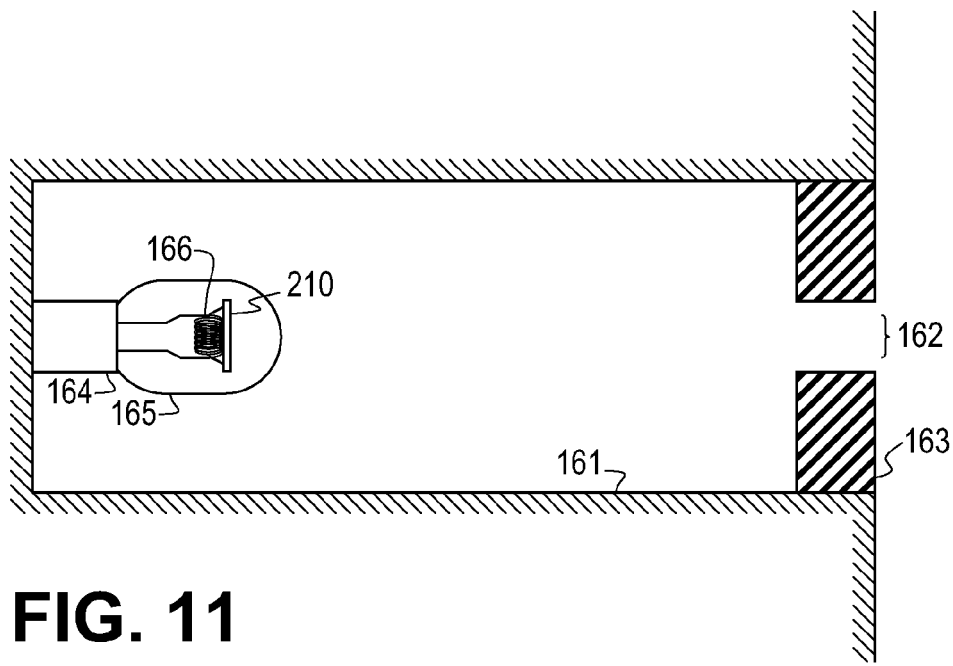
FIG. 11 shows a first embodiment of an enhanced light source.

Nevertheless, the present disclosure exploits this relationship by expanding the radiating area of a given light source, thereby enhancing the long-wavelength intensity that can be provided for a given input power. FIG. 11 shows a first embodiment of an enhanced light source. The source of FIG. 11 strongly resembles the baseline source of FIG. 6, but it includes a disk 210 in thermal contact with the filament 166. The disk can be any material that doesn't deform, melt or evaporate as the filament cycles between the ambient temperature and its operating temperature. A thermally conductive material such as a metal or a semiconductor can distribute the heat efficiently over the full surface of the disk, though caution should be taken to ensure that the disk does not allow electrical current to bypass the filament 166. By providing a larger radiating surface than that possessed by the filament alone, the disk 210 provides enhanced emissions in the near infrared. It is contemplated that the surface of the disk 202 may be corrugated, roughened, or otherwise patterned to increase the radiating surface area.

Figure 12:
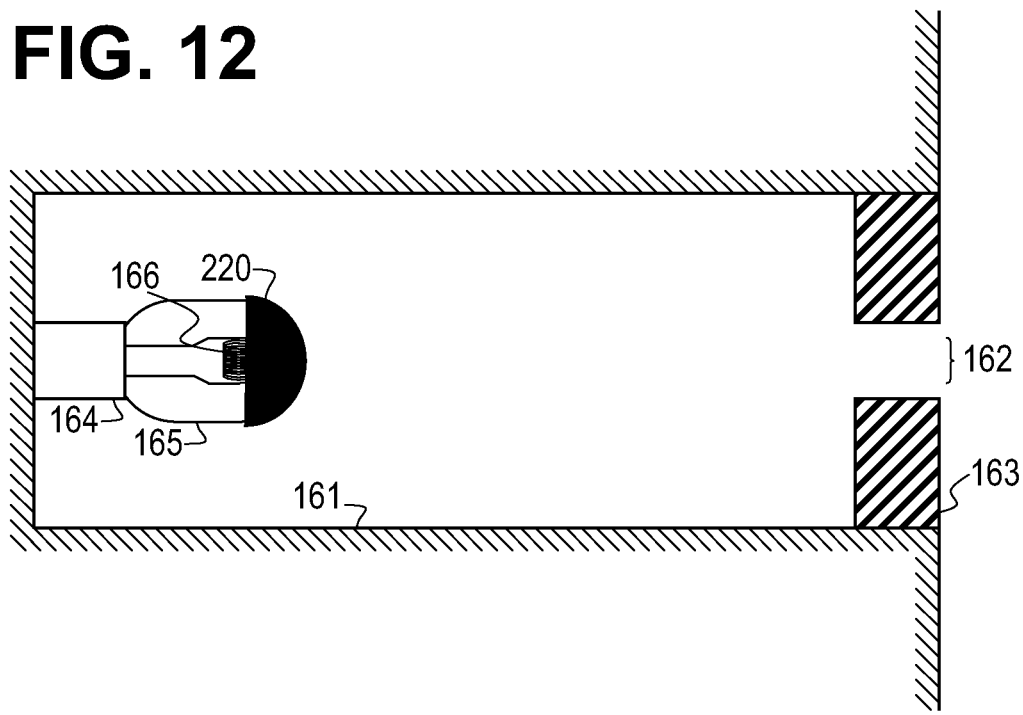
FIG. 12 shows a second embodiment of an enhanced light source.
Figure 13:
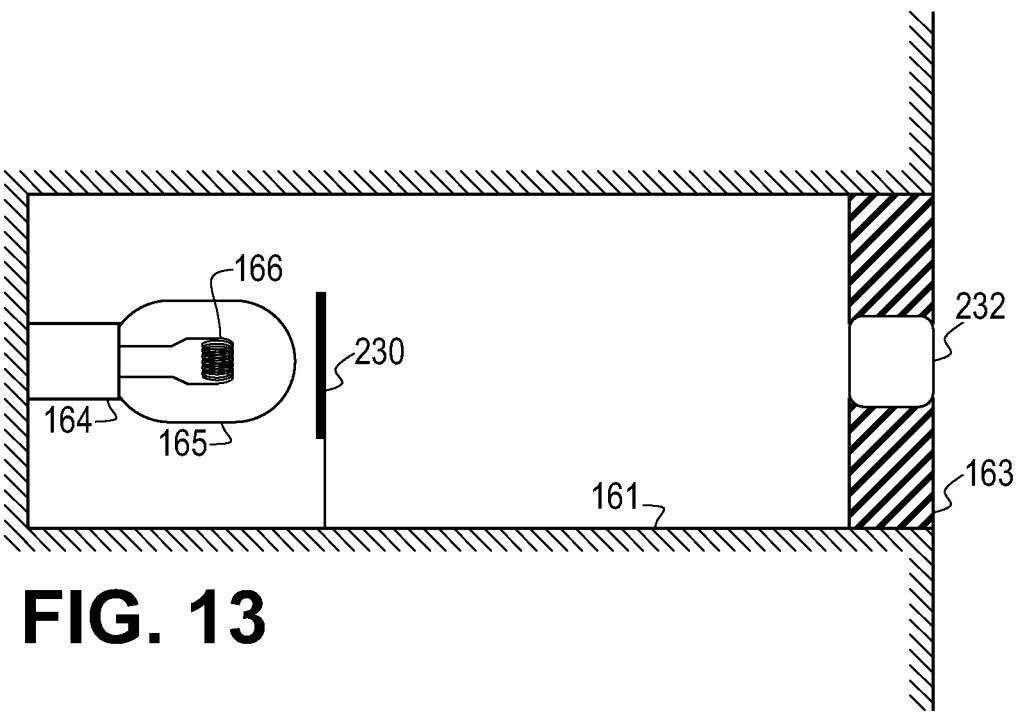
FIG. 13 shows a third embodiment of an enhanced light source.

It is not necessary that the enlarged radiating surface be in mechanical contact with the filament. As shown in FIG. 12, the light source can be provided with enhanced IR emission by providing the bulb envelope 165 with an opaque coating 220 that absorbs energy from filament 166 and re-radiates it over a larger surface area. To maximize the emitted light intensity, any other processes that tend to cool the coating 220 (e.g., thermal conduction, convection) should be minimized. For this reason, the coating 220 may be located on the inner surface of the bulb envelope 165. Alternatively, the compartment 161 may be evacuated or maintained at a relatively low air pressure. In addition, the compartment 161 may be heated and/or insulated to further reduce non-radiative cooling.

In yet another embodiment, an external occluding surface 230 is provided to absorb the emitted energy from the filament 166 and re-radiate it over a larger surface. As non-radiative cooling processes can become a significant factor in this design, the compartment is preferably sealed (with a window 232 in place of aperture 162) and evacuated. The supports for occluding surface 230 may be designed to minimize thermal conduction away from the surface 230, and the compartment 161 may be insulated.

FIGS. 14A and 14B show yet another embodiment of an enhanced light source in which the filament is replaced with an electron beam emitter 240. Electrons are drawn off the negatively-charged emitter 240 by an electrical field that then accelerates the electrons into a positively charged target 241, thereby heating it into incandescence. If desired, the necessary electric field magnitude can be reduced by heating the emitter 240. The target (also termed an anode) 241 can be made up of an array of tubes having open or closed ends. In one particular embodiment, the ends of the tubes nearest the emitter are closed, while the ends of the tubes furthest from the emitter are open. The large surface area of the anode 241 provides enhanced near infrared emission for a given input power. As shown in FIG. 14B, the tubes can have different diameters, different lengths, and even differently-shaped cross-sections to tailor their individual steady-state temperatures, thereby enabling some degree of customization of the light emission profile. Notably, when viewed from the distal end, the radiating surface area of the anode is a large fraction of the area enclosed by the bulb, e.g., greater than ⅓, or possibly greater than ½ or even in some cases exceeding 80%.

In each of the foregoing embodiments, the filament of the baseline source has either been occluded by, or replaced with, a larger radiator. The embodiment of FIGS. 15A and 15B takes a slightly different approach in which the filament is not blocked, but rather is augmented with some method for capturing and re-radiating light energy that would otherwise have been wasted. In the illustrated embodiment, a coating 250 is provided on the inner or outer surface of envelope 165 to absorb and re-radiate light over a larger surface area. However, the coating is not placed between the filament 166 and the aperture 162, but rather only coats the region around the bulb's base 164.

Figure 17:
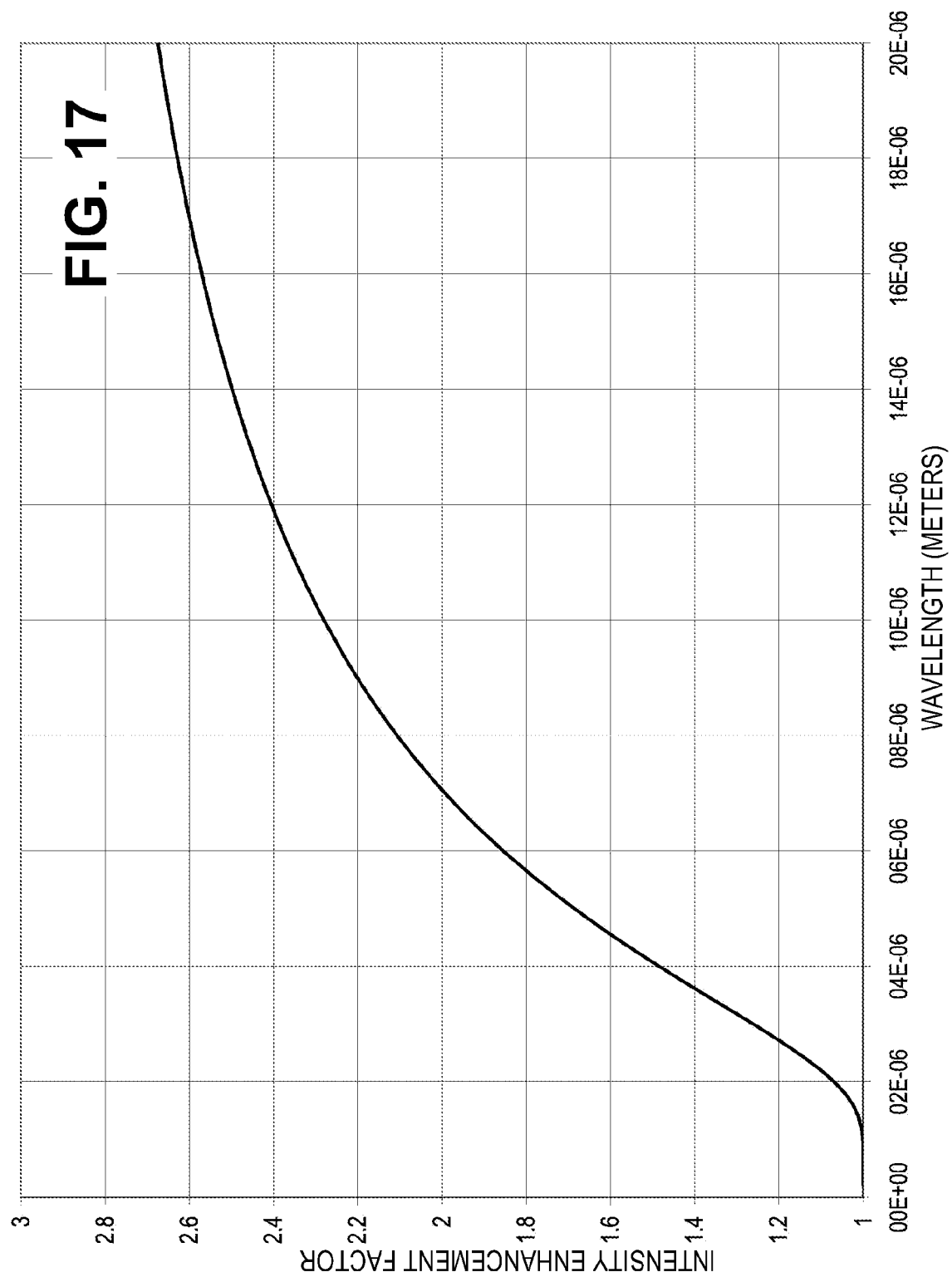
FIG. 17 shows the relative enhancement factor for the alternative enhancement approach.

The emission curves for this augmentation approach take on a different character than the enlargement approach discussed previously. FIG. 16, illustrates the relationship between three curves: the Planck's law emission curve for the baseline source at 3000 K, the Planck's law emission curve for a blackbody radiator at 1060 K, and the emission curve of a baseline source augmented by a blackbody re-radiator having an area six times the area of the original source. FIG. 17 shows the intensity enhancement factor for this example. The enhancement factor varies from unity at short wavelengths to about 3.12 at long wavelengths. At 12 microns, the enhancement factor is about 2.4, making this approach viable for tools having light source configurations that would otherwise waste a significant fraction of their emitted light.

Though the coating in the embodiments of FIGS. 15A-15B is continuous, this is not a requirement. As shown in FIG. 15C, the coating 251 can be patterned in a checkerboard fashion. Alternatively, stripes, rings, dots, or other shapes can be used to adjust the temperature and emission profile of the re-radiators. Such patterns can be used to partially occlude the filament and thereby provide a combination of the augmentation approach with the enlargement approach. Moreover, if the size of the re-radiating elements (or, in the case of tubes, the size of the tube opening) is reduced to the micron range (e.g., 1 to 100 microns), it is expected that those elements will exhibit resonance characteristics and preferentially emit light having wavelengths that are some integer fraction of twice the element diameter. The resulting emission curve for a given element is expected to be very narrow, though there is an opportunity for broadening by employing an irregular shape with different diameters. If re-radiating elements are provided with a distribution of sizes and shapes, the emission spectrum can be tailored to meet different design criteria. In particular, it is expected that the long-wavelength tail seen in blackbody radiation curves can be suppressed in favor of emission in the desired wavelength band from 1-20 microns.

Figure 18A:
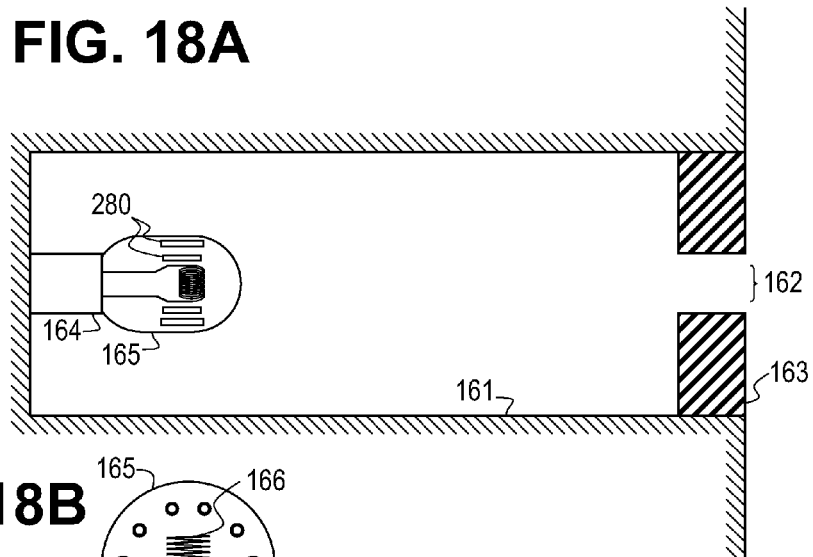
FIGS. 18A-B show a sixth embodiment of an enhanced light source.
Figure 18B:
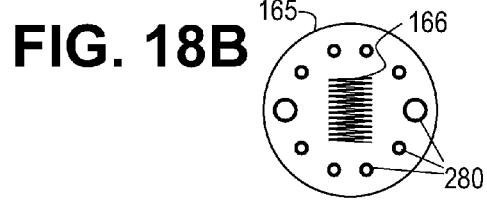
Figure 19A:
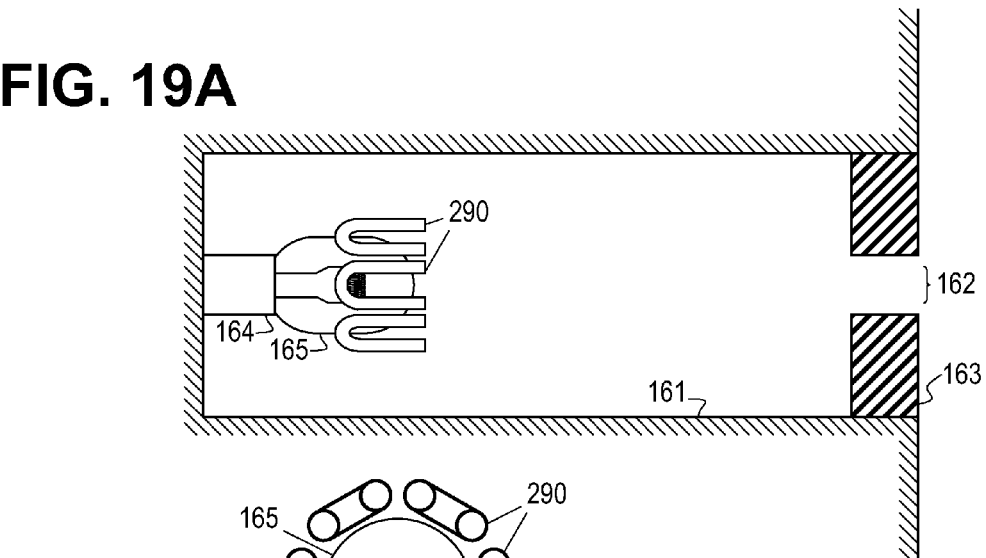
FIGS. 19A-B show a seventh embodiment of an enhanced light source.
Figure 19B:
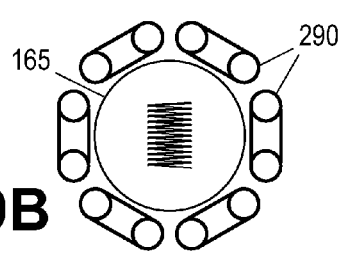
Figure 20A:
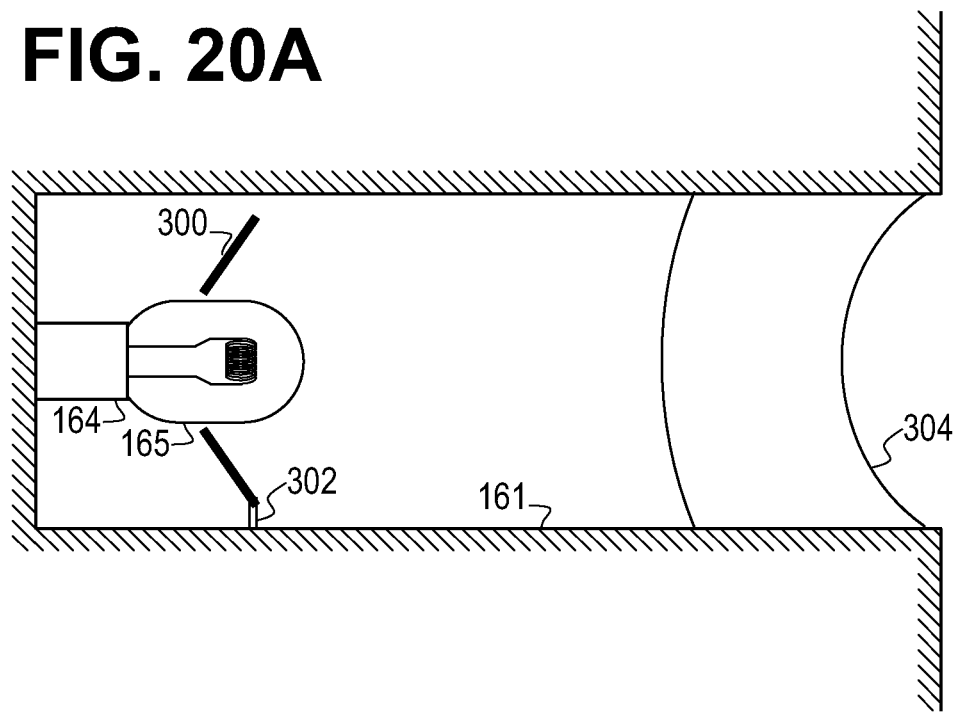
FIGS. 20A-20B show an eighth embodiment of an enhanced light source.
Figure 20B:
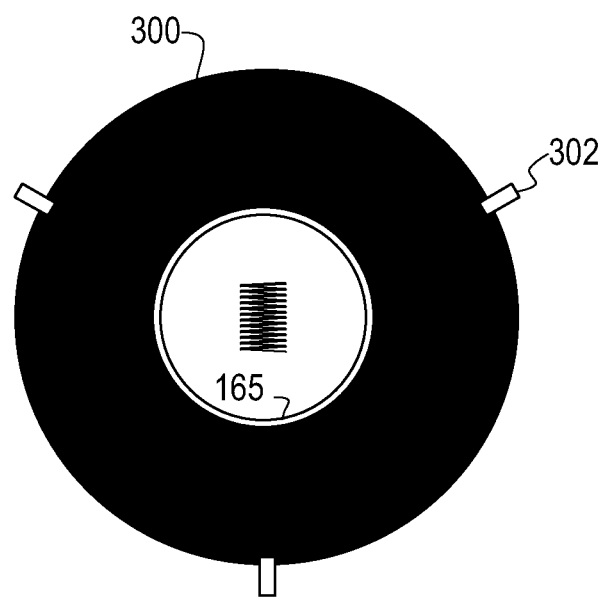

FIGS. 18A and 18B show an enhanced light source embodiment that augments the emission of filament 166 with an arrangement of re-radiator tubes 280 positioned around, but spaced away from, the filament. The length, diameter, cross-sectional shape, and spacing of the re-radiators can vary as desired to tune the temperature and emission profile. In this embodiment, the re-radiators are position inside the bulb envelope 165, whereas in the embodiment shown in FIGS. 19A and 19B, the re-radiators 290 are positioned outside the envelope 165. In this embodiment, the re-radiator tubes have been formed into U-shapes, with the open ends of the "U" oriented towards the aperture 162. Finally, FIGS. 20A-20B show an enhanced light source embodiment where a collar 300 is held in place around the bulb envelope 165 by supports 302. The collar 300 absorb and re-radiate light from the filament over a much larger surface area. The increased diameter of the light source may motivate the use of a lens 304 to provide a tighter collimation of the light beam.

It is noted that the augmentation approach provides an opportunity for increased control over the spatial distribution of emitted wavelengths. Those embodiments having re-radiators around the periphery of the filament will provide the enhanced IR emission around the periphery of the collimated beam. Such improved control over the spatial distribution of wavelength provides opportunities for optimizing the optics to the different wavelengths. In particular, because the refractive index of most materials varies with the frequency of the light passing through them, the shape of the optical elements can be tailored differently at the collimated beam edges than at the center to, e.g., achieve a tighter focus in the sample chamber, or to achieve a better dispersal of wavelengths over a detector array. Alternatively, the optical elements can be formed from metamaterials offering an index of refraction which can be tuned to suit the spatially-dependent requirements of the beam.

Numerous variations and modifications will become apparent to those skilled in the art once the above disclosure is fully appreciated. For example, the illustrative embodiments discussed above have focused on light sources that include bulb-shaped envelopes, but it is recognized that other envelope shapes are popular and can be used. It is intended that the following claims be interpreted to embrace all such variations and modifications.

What is claimed is:

1. A light source having enhanced long-wavelength emission, comprising: a base; a filament mounted to the base to receive electrical current and become resistively heated; a bulb mounted to the base to enclose the filament in a selected environment; and a radiator element mounted within the bulb to be heated by the filament and radiate infrared light, wherein said radiator element has a surface area larger than a surface area of said filament and wherein the radiator element comprises an arrangement of tubes positioned circumferentially around the filament and oriented parallel and not coaxial to each other or to a central axis of the light source.

2. The light source of claim 1, wherein the selected environment is a vacuum.

3. The light source of claim 1, wherein the selected environment comprises at least one of an inert gas and a halogen.

4. The light source of claim 1, wherein the radiator element contacts the filament.

5. The light source of claim 1, wherein the tubes are spaced apart from each other.

6. The light source of claim 1, wherein at least one of the tubes has a different diameter than another one of the tubes.

7. A long-wavelength light source that comprises: an envelope containing a vacuum; a cathode that emits electrons; and an anode that is heated by a stream of said electrons, wherein as viewed from at least one direction, the anode has a radiating area greater than one-third of the area enclosed by the envelope;

wherein the anode comprises an arrangement of adjacent parallel tubes positioned circumferentially around the cathode and not coaxial to each other or to a central axis of the cathode.

8. The light source of claim 7, wherein ends of said parallel tubes distal from the cathode are open.

9. The light source of claim 7, wherein at least one of the parallel tubes has a different diameter from another one of the tubes.

\* \* \* \* \*